US005571880A

United States Patent [19]

Alt et al.

[11] Patent Number: 5,571,880
[45] Date of Patent: Nov. 5, 1996

[54] ORGANOMETALLIC FLUORENYL COMPOUNDS AND USE THEREOF IN AN ALPHA-OLEFIN POLYMERIZATION PROCESS

[75] Inventors: Helmut G. Alt, Bayreuth, Germany;
Syriac J. Palackal, Bartlesville, Okla.;
Roland Zenk, Bayreuth, Germany; M. Bruce Welch, Bartlesville, Okla.;
Michael Schmid, Bayreuth, Germany

[73] Assignee: Phillips Petroleum Company, Bartlesville, Okla.

[21] Appl. No.: 192,223

[22] Filed: Feb. 3, 1994

Related U.S. Application Data

[63] Continuation-in-part of Ser. No. 734,853, Jul. 23, 1991, Pat. No. 5,436,305, which is a continuation-in-part of Ser. No. 697,363, May 9, 1991, Pat. No. 5,191,132, and a continuation-in-part of Ser. No. 3,221, Jan. 7, 1993, Pat. No. 5,406,013, which is a continuation of Ser. No. 697,363, May 9, 1991, Pat. No. 5,191,132, and a continuation-in-part of Ser. No. 64,630, May 20, 1993, Pat. No. 5,401,817, which is a continuation-in-part of Ser. No. 734,853, Jul. 23, 1991, Pat. No. 5,436,305, and a continuation-in-part of Ser. No. 984,054, Nov. 30, 1992, Pat. No. 5,393,911, which is a continuation-in-part of Ser. No. 697,363, May 9, 1991, Pat. No. 5,191,132.

[51] Int. Cl.⁶ .................. C08F 4/642; C07F 17/00
[52] U.S. Cl. .................. 526/160; 526/170; 526/351; 526/943; 502/117; 502/152; 502/154; 556/43; 556/52; 556/53; 556/58
[58] Field of Search .................. 526/160, 170, 526/943; 556/43, 52, 53, 58; 502/117, 152, 154

[56] References Cited

U.S. PATENT DOCUMENTS

| | | | |
|---|---|---|---|
| 3,980,713 | 9/1976 | Matsunaga et al. | 260/612 R |
| 4,760,194 | 7/1988 | Phillips et al. | 568/454 |
| 4,892,851 | 1/1990 | Ewen et al. | 502/104 |
| 5,036,034 | 7/1991 | Ewen | 502/117 |
| 5,087,677 | 2/1992 | Brekner et al. | 526/160 |
| 5,132,381 | 7/1992 | Winter et al. | 526/160 |
| 5,158,920 | 10/1992 | Razavi | 502/152 |
| 5,162,278 | 11/1992 | Razavi | 502/152 |
| 5,225,501 | 7/1993 | Fujita et al. | 526/127 |
| 5,237,116 | 8/1993 | Corley | 585/411 |
| 5,308,817 | 5/1994 | Reddy et al. | 502/117 |
| 5,391,789 | 2/1995 | Rohrmann | 556/11 |
| 5,436,305 | 7/1995 | Alt et al. | 526/160 |

FOREIGN PATENT DOCUMENTS

| | | |
|---|---|---|
| 498675A2 | 8/1992 | European Pat. Off. . |
| 528287A1 | 2/1993 | European Pat. Off. . |
| 574370A1 | 12/1993 | European Pat. Off. . |
| 0577581A2 | 1/1994 | European Pat. Off. . |
| 04-69394 | 3/1992 | Japan . |

OTHER PUBLICATIONS

Chem. Abstract, 120:9147g.
European Search Report.
Organic Synthesis, vol. 58, (1978), pp. 127–133.
J. Org. Chem., vol. 41, (1976), pp. 2252–2255.
Bulletin of the Chemical Society of Japan, vol. 49, (1976), pp. 1958–1969.
Pure and Appl. Chem., vol. 52, (1980), pp. 669–679.

*Primary Examiner*—Fred Teskin
*Attorney, Agent, or Firm*—Edward L. Bowman

[57] ABSTRACT

Fluorenyl-containing metallocenes are disclosed along with methods for making the metallocenes. Also disclosed are methods for using the metallocenes as polymerization catalysts. In addition, polymers resulting from such polymerizations are disclosed.

22 Claims, No Drawings

ORGANOMETALLIC FLUORENYL COMPOUNDS AND USE THEREOF IN AN ALPHA-OLEFIN POLYMERIZATION PROCESS

This application is a continuation-in-part of U.S. patent application Ser. No. 07/734,853 filed Jul. 23, 1991, now U.S. Pat. No. 5,436,305, as a continuation-in-part of U.S. patent application Ser. No. 07/697,363 filed May 9, 1991, now U.S. Pat. No. 5,191,132. This application is also a continuation-in-part of U.S. patent application Ser. No. 08/003,221 filed Jan. 7, 1993, now U.S. Pat. No. 5,406,013, which was a continuation of the same U.S. patent application Ser. No. 07/697,363 filed May 9, 1991, now U.S. Pat. No. 5,191,132. This application is also a continuation-in-part of U.S. patent application Ser. No. 08/064,630 filed May 20, 1993, now U.S. Pat. No. 5,401,817, as a continuation-in-part of the aforementioned U.S. patent application Ser. No. 07/734,853 filed Jul. 23, 1991, now U.S. Pat. No. 5,436,305. This application is further a continuation-in-part of U.S. patent application Ser. No. 07/984,054 filed Nov. 30, 1992, now U.S. Pat. No. 5,393,911, as a continuation-in-part of the aforementioned U.S. patent application Ser. No. 07/697,363 filed May 9, 1991, now U.S. Pat. No. 5,191,132. The disclosures of the above-mentioned applications are incorporated herein by reference.

This invention relates to organometallic compounds. More specifically, this invention relates to organometallic compounds containing at least one fluorenyl ligand. In another aspect, this invention relates to polymerization catalyst systems which contain organometallic fluorenyl compounds. In still another aspect, this invention relates to a method for polymerizing olefins using such organometallic fluorenyl compounds and to the polymers resulting from such polymerizations.

BACKGROUND OF THE INVENTION

Since the discovery of ferrocene in 1951, a number of metallocenes have been prepared by the combination of compounds having cyclopentadienyl structure with various transition metals. The term "cyclopentadienyl structure" as used herein refers to the following structure.

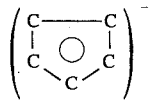

The term "cyclopentadiene-type compounds" as used herein refers to compounds containing the cyclopentadiene structure. Examples include unsubstituted cyclopentadiene, unsubstituted indene, unsubstituted fluorene, and substituted varieties of such compounds. Also included is tetrahydro indene. Thus polycyclic cyclopentadiene compounds are included within the term.

Many of the cyclopentadiene-type metallocenes have been found useful in catalyst systems for the polymerization of olefins. It has been noted in the art that variations in the chemical structure of such cyclopentadienyl-type metallocenes can have significant effects upon the suitability of the metallocene as a polymerization catalyst. For example, the size and substitutions on cyclopentadienyl-type ligands has been found to affect the activity of the catalyst, the stereoselectivity of the catalyst, the stability of the catalyst, and other properties of the resulting polymer; however, the effects of various substituents is still largely an empirical matter, that is, experiments must be conducted in order to determine just what effect a particular variation will have upon a particular type of cyclopentadienyl-type metallocene. Some examples of some cyclopentadienyl-type metallocenes are disclosed in U.S. Pat. Nos. 4,530,914; 4,808,561; and 4,892,851, the disclosures of which are incorporated herein by reference.

While there are references in the prior art which have envisioned metallocenes containing fluorenyl groups, only a very limited number of fluorenyl-containing metallocenes have actually been prepared prior to the present invention. The Journal of Organometallic Chemistry, Vol. 113, pages 331–339 (1976), the disclosure of which is incorporated herein by reference, discloses preparing bis-fluorenyl zirconium dichloride and bis-fluorenyl zirconium dimethyl. U.S. Pat. No. 4,892,851 and the New Journal of Chemistry, Vol. 14, pages 499–503, dated 1990, the disclosures of which are incorporated herein by reference, each disclose preparing a metallocene from the ligand 1-(cyclopentadienyl)-1-(fluorenyl)-1, 1-dimethylmethylene. The New Journal of Chemistry article also discloses preparing a similar compound in which the cyclopentadienyl radical has a methyl substituent in the number 3 position. The term fluorenyl as used herein refers to 9-fluorenyl unless indicated otherwise.

An object of the present invention is to provide certain new fluorenyl-containing metallocenes. Another object of the present invention is to provide a method for preparing new fluorenyl-type metallocenes. Still another object of the present invention is to provide polymerization catalysts employing fluorenyl-type metallocenes. Still yet another object of the present invention is to provide processes for the polymerization of olefins using fluorenyl-type metallocene catalyst systems. Still yet another object of the present invention is to provide polymers produced using such fluorenyl-containing metallocene catalysts.

SUMMARY OF THE INVENTION

In accordance with the present invention, there are provided new metallocenes of the formula $R''_x(FlR_n)(CpR_m)MeQ_k$ wherein Fl is a fluorenyl radical, Cp is a cyclopentadienyl, indenyl, tetrahydro indenyl, or fluorenyl radical, each R is the same or different and is a halide or an organo radical having 1 to 20 carbon atoms, R" is a structural bridge linking $(FlR_n)$ and $(CpR_m)$, Me is metal selected from the group consisting of IVB, VB, and VIB metals of the Periodic Table, each Q is the same or different and is selected from the group consisting of hydrocarbyl or hydrocarbyloxy radicals having 1 to 20 carbon atoms and halogens, x is 1 or 0, k is a number sufficient to fill out the remaining valences of Me, n is a number in the range of 0 to 7, m is a number in the range of 0 to 7, further characterized by the fact that if $(CpR_m)$ is unsubstituted fluorenyl and x is 0, then n is 1 to 7, and if $(CpR_m)$ is unsubstituted cyclopentadienyl or 3-methylcyclopentadienyl and R" is 1,1-dimethyl-methylene, then n=1 to 7.

In accordance with another aspect of the present invention, there is provided a method for forming fluorenyl-containing metallocenes comprising reacting an alkali metal salt of the selected fluorenyl compound with a transition metal compound of the formula MeQk in the presence of a non-halogenated solvent for the fluorenyl salt which solvent is non-coordinating with respect to the transition metal compound.

In accordance with still another aspect of the present invention, there is provided a process for the polymerization of olefins comprising contacting said olefins under suitable reaction conditions with a catalyst system comprising a fluorenyl-containing metallocene as described above in combination with a suitable organoaluminum co-catalyst.

Still further in accordance with the present invention there is provided the polymer products resulting from such polymerizations.

DETAILED DESCRIPTION OF THE INVENTION

The novel metallocenes provided in accordance with the present invention fall into two broad general categories. One category involves metallocenes in which a fluorenyl radical, either substituted or unsubstituted, is bonded to another cyclopentadienyl-type radical by a bridging structure R". These metallocenes are referred to herein as bridged metallocenes. The other category deals with metallocenes which are unbridged, that is the fluorenyl radical ligand and the other cyclopentadienyl-type ligands are bound to the metal but not to each other. These metallocenes are referred to as unbridged metallocenes. Methods for preparing fluorenyl-containing cyclopentadiene-type compounds which can be used in making the metallocenes are disclosed in the aforementioned U.S. patent application Ser. No. 697,363.

The metal, Me is selected from the group IV, VB, or VIB metals of the Periodic Table. The currently preferred metals include titanium, zirconium, hafnium, chromium, and vanadium. The R" can be selected from any suitable bridging structure. Typical examples include hydrocarbyl and heteroatom containing alkylene radicals containing 1 to 20 carbon atoms, especially 2 to 20 carbon atoms; germanium: silicon; phosphorus; boron; aluminum; tin; oxygen; nitrogen; and the like. The bridge can even be a cyclic hydrocarbyl structure. Some examples include cyclopentylidene, adamantylidene, cyclohexenylidene, cyclohexylidene, indenylidene, and the like. The R" bridge when hydrocarbyl can be aromatic in nature, such as a phenyl substituted alkylene; however, the currently preferred modes employ aliphatic alkylene bridges. The currently most preferred bridges are hydrocarbyl or heteroatom containing alkylene radical having 1 to 6 carbon atoms. In an especially preferred embodiment k is equal to the valence of Me minus 2.

The substituents R can be selected from a wide range of substituents. In the preferred embodiments the substituents R are each independently selected from halides or hydrocarbyl radicals having 1 to 20 carbon atoms. In a particularly preferred embodiment, the hydrocarbyl radicals R are alkyl, aryl, or arylalkyl radicals. More preferably the alkyl R radicals have 1 to 5 carbon atoms.

Each Q is a hydrocarbyl radical such as, for example, aryl, alkyl, alkenyl, alkaryl, or arylalkyl radical having from 1 to 20 carbon atoms, hydrocarbyloxy radicals having 1 to 20 carbon atoms, or halogen. Exemplary Q hydrocarbyl radicals include methyl, ethyl, propyl, butyl, amyl, isoamyl, hexyl, isobutyl, heptyl, octyl, nonyl, decyl, cetyl, 2-ethylhexyl, phenyl, and the like. Exemplary halogen atoms include chlorine, bromine, fluorine, and iodine and of these halogen atoms, chlorine is currently preferred. Exemplary hydrocarboxy radicals include methoxy, ethoxy, propoxy, butoxy, amyloxy, and the like.

Illustrative, but non-limiting examples of unbridged metallocenes falling within the scope of the above formula include bis(1-methyl fluorenyl) zirconium dichloride, bis(1-methyl fluorenyl) zirconium dimethyl, bis(1-methyl fluorenyl) hafnium dichloride, bis(1-butyl fluorenyl)zirconium dichloride, bis(2-ethyl fluorenyl) zirconium dichloride, bis(4-methyl fluorenyl)zirconium dichloride, bis(4-methyl fluorenyl)hafnium dichloride, bis(2-t-butyl fluorenyl) zirconium dichloride, bis(4-t-butyl fluorenyl)zirconium dichloride, bis(2,7-di-t-butyl fluorenyl)zirconium dichloride, bis(2,7-di-t-butyl-4-methyl fluorenyl)zirconium dichloride, and the like.

Illustrative, but non-limiting examples of metallocenes containing bridged fluorenyl ligands include for example (1,1-difluorenylmethane)zirconium dichloride, (1,2-difluorenyl)ethane zirconium dichloride, (1,3-difluorenylpropane)zirconium dichloride, (1,2-difluorenylethane)hafnium dichloride, (1,3-difluorenylpropane)hafnium dichloride, (1-fluorenyl-2-methyl-2-fluorenylethane)zirconium dichloride, dimethylsilyldifluorenyl zirconium dichloride, (1,2-di(1-methyl fluorenyl)ethane)zirconium dichloride, (1,2-di(1-methyl fluorenyl) ethane) hafnium dichloride, (1,2-di(2-ethyl fluorenyl)ethane)zirconium dichloride, (1,2-di(2-t-butyl fluorenyl)ethane)zirconium dichloride, (1,2-di(2-t-butyl fluorenyl)ethane)hafnium dichloride, (1,2-di(1-t-butyl fluorenyl)ethane) zirconium dichloride, (1,2-di(4-methyl fluorenyl ethane) zirconium dichloride, (1,2-di(4-methyl fluorenyl)ethane) hafnium dichloride, (1,2-di(4-t-butyl fluorenyl)ethane) zirconium dichloride, 1-(fluorenyl)-1-(cyclopentadienyl)methane zirconium dichloride, 1-(fluorenyl)-1-(cyclopentadienyl)methane hafnium dichloride, 1-(2,7-di-t-butyl fluorenyl)-1-(cyclopentadienyl)methane zirconium dichloride, 1-(fluorenyl)-2-(cyclopentadienyl)ethane zirconium dichloride, (1-fluorenyl-2-(3-methyl cyclopentadienyl)ethane)zirconium dichloride, (1-fluorenyl-2-indenyl ethane)zirconium dichloride, (1-fluorenyl-2-indenyl ethane)hafnium dichloride, (1-fluorenyl-2-methyl-2-indenyl ethane)zirconium dichloride, (1-fluorenyl-2-methyl-2-indenyl ethane)hafnium dichloride, (bis-fluorenylmethane)vanadium dichloride, (1,2-difluorenyl ethane)vanadium dichloride, (1-fluorenyl-1-cyclopentadienyl methane) zirconium trichloride, (1-fluorenyl-2-methyl-2-(3-methyl cyclopentadienyl)ethane)zirconium dichloride, (1-(1-methyl fluorenyl)-2-(4-methyl fluorenyl)ethane)zirconium dichloride, (1-(2,7-di-t-butyl fluorenyl)-2-(fluorenyl)ethane)zirconium dichloride, (1,2-di(2,7-di-t-butyl-4-methyl fluorenyl)ethane)zirconium dichloride, (1-(2,7-dimethylvinyl fluorenyl)-1-(cyclopentadienyl)-1,1-dimethyl methane)zirconium dichloride, which could also be called 1-(2,7-di-isopropenyl fluorenyl)-1-(cyclopentadienyl)-1,1-dimethyl methane) zirconium dichloride, 1-(2,7-dimesityl fluorenyl)-1-cyclopentadienyl)-1, 1-dimethyl methane) zirconium dichloride, 1-(2,7-dimethoxy fluorenyl)-1-(cyclopentadienyl)-1,1-diphenyl methane) zirconium dichloride, 1-(2,7-dimethoxy fluorenyl)-1-(cyclopentadienyl)-1, 1-dimethyl methane) zirconium dichloride, 1-(2,7-diphenyl fluorenyl)-1-(cyclopentadienyl)-1-phenyl methane) zirconium dichloride, 1-(2,7-dibromo fluorenyl)-1-(cyclopentadienyl)-1-methyl methane) zirconium dichloride, 1-(2,7-dimesityl fluorenyl)-1-(cyclopentadienyl)cyclopentane) zirconium dichloride, 1-(2,7 dimethylfluorenyl)-1-(cyclopentadienyl) methane zirconium dichloride, 1-(2-7-diphenylfluorenyl)-1-(cyclopentadienyl) indanylidene zirconium dichloride, 1-(2,7-di-t-butyl fluorenyl)-1-(cyclopentadienyl) cyclopentylidene zirconium dichloride, 1-(2,7 dibromofluorenyl)-1-(cyclopentadienyl) methane zirconium dichloride, 1-(2,7-dimethylfluorenyl)-1-(cyclopentadienyl))-1, 1-dimethyl methane zirconium dichloride, and 1-(2,7 bis(dimethyl phenyl carbyl) fluorenyl)-1-(cyclopentadienyl) diphenylmethane zirconium dichloride and the like.

Particularly preferred metallocene species include bridged and unbridged metallocenes containing at least one substituted fluorenyl radical, i.e., there is at least one FlRn wherein n is 1 to 7. In an especially preferred embodiment bridged fluorenyl compounds of the formula (FlRn)R"(CpRm) are used wherein Fl, R, R", and m are as defined above, and where n is 1 to 7, most preferably 1 to 4, and especially 2.

Another particularly preferred type of metallocenes are bridged metallocenes containing at least one symmetrically substituted fluorenyl radical. The term symmetrically substituted as used herein refers to fluorenyl radical having substituents on opposite portions of the fluorenyl radical, such as for example 2,7-dialkylfluorenyl; 2,7-dicycloalkenylfluorenyl; 3,6-dialkylfluorenyl; 2,7-dihalo fluorenyl; 2,7-diarylfluorenyl; 1,8-dialkylfluorenyl; 4,5-dialkylfluorenyl; 2,7-diarylalkylfluorenyl; and the like. Most preferably the substituents on the fluorenyl are the same. The currently preferred alkyl substituents have 1 to 20 carbon atoms, more preferably 1 to 6 carbon atoms, and most preferrably 1 to 4 carbon atoms. The currently most preferred halide substituents include those having 6 to 20 carbon atoms, with those having 6 to 10 carbon atoms generally more preferred. Likewise the arylalkyl substituents can contain 7 to 20 carbon atoms, more commonly 7 to 10 carbon atoms. It should be recognized that in certain instances if the bridge and the substituents on the fluorenyl are particularly bulky it may be difficult to prepare the ligand, the dialkyl salt, or the metallocene.

The inventive metallocenes as well as related metallocenes can be prepared by reacting an alkali metal salt of the bridged fluorenyl compounds with a suitable transition metal compound in a suitable solvent under suitable reaction conditions.

Techniques for preparing the bridged ligands are disclosed in U.S. Pat. No. 5,191,132 and the aforementioned U.S. patent application Ser. No. 08/064,630 and 07/984,054. Methylene bridged ligands can be made by using 6 or 6,6 substituted fulvenes. Examples of fulvene reactions are disclosed in U.S. Pat. No. 4,892,851 and in *J. Organomet. Chem.*435, 299–310 (1992). In general the technique involves reacting an alkali metal salt of the 2,7-substituted fluorene with the selected fulvene type compound. The 6,6-diphenyl fulvenes can be prepared by reacting a suitable aryl bromide, i.e. phenyl bromide, p-tolyl bromide, p-fluorophenyl bromide, or p-t-butylphenyl bromide, with magnesium to form a Grignard reagent. Then the dropwise addition of methyl formate and subsequent hydrolysis results in the formation of the diarylcarbinol. The diarylcarbinol can then be oxidized smoothly to give the corresponding substituted benzophenone, preferably using sulfuric acid and chromic acid. The resulting substituted benzophenone can then be reacted with cyclopentadiene in ethanol containing sodium to yield the 6,6-substituted fulvene.

A variation of this technique involves the production of indanyl fulvene (which can also be called indanylidene fulvene) by reacting 1-indanone with cyclopentadiene in the presence of ethanol and sodium ethoxide. The indanyl fulvene is particularly useful in that it can be reacted with the alkali metal salt of a fluorene compound to yield an indanyl bridged fluorenyl cyclopentadienyl compound. An example would be 1-(2,7-diphenylfluorenyl)-1-(cyclopentadienyl) indanylidene.

The symmetrically substituted fluorenyl compounds needed to make the bridged ligands can be prepared using procedures generally known in the prior art. Some particularly desirable techniques for forming certain of the substituted fluorenyl compounds will be described in further detail in what follows.

The term transition metal compound as used herein includes compounds of the formula MeQk wherein Me, Q, and k are as defined above. Some non-limiting examples include zirconium tetrachloride, hafnium tetrachloride, titanium tetrachloride, cyclopentadienyl zirconium trichloride, fluorenyl cyclopentadienyl zirconium dichloride, 3-methylcyclopentadienyl zirconium trichloride, indenyl cyclopentadienyl zirconium dichloride, 4-methyl fluorenyl zirconium trichloride, and the like.

Metallocenes in which Q is other than a halogen can be readily prepared by reacting the halide form of the metallocene with an alkali metal salt of the hydrocarbyl or hydrocarbyloxy radical under conditions as have been used in the past for forming such ligands in prior art metallocenes. See, for example, the aforemention J. Org. Chem. 113, 331–339 (1976). Another approach involves reacting a compound of the formula MeQk wherein at least one Q is hydrocarbyl or hydrocarbyloxy with the alkali metal salt of the bridged or unbridged fluorenyl compound.

One embodiment of the present invention involves carrying out the reaction of the fluorenyl-containing salt and the transition metal compound in the presence of a liquid diluent which is non-halogenated and non-coordinating toward the transition metal compound. Examples of such suitable liquid include hydrocarbons such as toluene, pentane, or hexane as well as non-cyclic ether compounds such as diethylether. It has been found that the use of such non-halogenated non-coordinating solvents generally allows one to obtain large amounts of substantially pure metallocenes and in a more stable form; and also often allows the reaction to be conducted under higher temperature conditions, than when THF is used as the diluent. In an especially preferred embodiment the fluorenyl-containing salt used as a ligand is also prepared in a liquid diluent that is non-halogenated and non-coordinating toward the transition metal.

The formation of the alkali metal salt of the bridged or unbridged fluorenyl compound can be formed using generally any technique known in the art. For example, such can be prepared by reacting an alkali metal alkyl with the cyclopentadienyl type compounds or the bridged compounds having two cyclopentadienyl-type radicals per molecule. The molar ratio of the alkali metal alkyl to the cyclopentadienyl type radicals present can vary, generally however, the ratio would be in the range of about 0.5/1 to about 1.5/1, still more preferably about 1/1. Typically, the alkali metal of the alkali metal alkyl would be selected from sodium, potassium, and lithium, and the alkyl group would have 1 to 8 carbon atoms, more preferably 1 to 4 carbon atoms. Preferably, if the fluorenyl salt is formed using tetrahydrofuran (THF) as the liquid solvent, the salt is isolated and substantially all of the THF is removed before the salt is contacted with the transition metal halide. The molar ratio of the bridged or unbridged fluorenyl compound to the transition metal compound can vary over a wide range depending upon the results desired. Typically, however, when an unbridged fluorenyl compound is used, the molar ratio of the unbridged fluorenyl compound to the transition metal compound is in the range of from about 1 to 1 to about 2 to 1 and when a bridged fluorenyl compound is used the molar ratio of the bridged fluorenyl compound to the transition metal compound is about 1 to 1.

The resulting metallocene can be recovered and purified using conventional techniques known in the art such as filtration, extraction, crystallization, and re-crystallization. It is generally desirable to recover the metallocene in a form that is free of any substantial amount of by-product impurities. Accordingly, recrystallization and fractional crystallization to obtain relatively pure metallocens is desirable. Dichloromethane has been found to be particularly useful for such recrystallizations. As a general rule, it has been found that the metallocenes based on unbridged fluorenyl compounds are less stable than the metallocene compounds formed from bridged fluorenyl compounds. Since the stability of the various metallocenes varies, it is generally desirable to use the metallocenes soon after their preparation or at least to store the metallocene under conditions favoring their stability. For example the metallocenes can generally be stored at low temperature, i.e. below 0° C. in the absence of oxygen or water.

The resulting fluorenyl containing metallocenes can be used in combination with a suitable co-catalyst for the polymerization of olefinic monomers. In such processes the metallocene or the co-catalyst can be employed on a solid insoluble particulate support.

Examples of suitable co-catalysts include generally any of those organometallic co-catalysts which have in the past been employed in conjunction with transition metal containing olefin polymerization catalysts. Some typical examples include organometallic compounds of metals of Groups IA, IIA, and IIIB of the Periodic Table. Examples of such compounds have included organometallic halide compounds, organometallic hydrides and even metal hydrides. Some specific examples include triethyl aluminum, triisobutyl aluminum, diethyl aluminum chloride, diethyl aluminum hydride, and the like. Other examples of known cocatalysts include the use of a stable non-coordinating counter anion techniques such as disclosed in U.S. Pat. No. 5,155,080, e.g. using triphenyl carbenium tetrakis (pentafluorophenyl) boronate. Another example would be the use a a mixture of trimethylaluminum and dimethylfluoroaluminum such as disclosed by Zambelli et, *Macromolecules*, 22, 2186 (1989). In such processes the metallocene or the co-catalyst can be employed on a solid insoluble support.

The currently most preferred co-catalyst is an aluminoxane. Such compounds include those compounds having repeating units of the formula

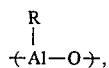

where R is an alkyl group generally having 1 to 5 carbon atoms. Aluminoxanes, also sometimes referred to as poly-(hydrocarbyl aluminum oxides) are well known in the art and are generally prepared by reacting an organo hydrocarbylaluminum compound with water. Such a preparation techniques are disclosed in U.S. Pat. Nos. 3,242,099 and 4,808,561, the disclosures of which are incorporated herein by reference. The currently preferred co-catalysts are prepared either from trimethylaluminum or triethylaluminum, sometimes referred to as poly(methyl aluminum oxide) and poly(ethyl aluminum oxide), respectively. It is also within the scope of the invention to use an aluminoxane in combination with a trialkylaluminum, such as disclosed in U.S. Pat. No. 4,794,096, the disclosure of which is incorporated herein by reference.

The fluorenyl-containing metallocenes in combination with the aluminoxane co-catalyst can be used to polymerize olefins. Generally such polymerizations would be carried out in a homogeneous system in which the catalyst and co-catalyst were soluble; however, it is within the scope of the present invention to carry out the polymerizations in the presence of supported forms of the catalyst and/or co-catalyst in a slurry or gas phase polymerization. It is within the scope of the invention to use a mixture of two or more fluorenyl-containing metallocenes or a mixture of an inventive fluorenyl-containing metallocene with one or more other cyclopentadienyl-type metallocenes.

The fluorenyl-containing metallocenes when used with aluminoxane are particularly useful for the polymerization of mono-unsaturated aliphatic alpha-olefins having 2 to 10 carbon atoms. Examples of such olefins include ethylene, propylene, butene-1, pentene-1, 3-methylbutene-1, hexene-1, 4-methylpentene-1, 3-ethylbutene-1, heptene-1, octene-1, decene-1, 4,4-dimethyl-1-pentene, 4,4-diethyl-1-hexene, 3-4-dimethyl-1-hexene, and the like and mixtures thereof. The catalysts are particularly useful for preparing copolymers of ethylene or propylene and generally a minor amount, i.e. about 20 to 10 mole percent, more commonly about 12 mole percent, still more typically less than about 10 mole percent, of the higher molecular weight olefin.

The polymerizations can be carried out under a wide range of conditions depending upon the particular metallocene employed, and the results desired. Examples of typical conditions under which the metallocenes can be used in the polymerization of olefins include conditions such as disclosed in U.S. Pat. Nos. 3,242,099; 4,892,851; and 4,530,914; the disclosures of which are incorporated herein by reference. It is considered that generally any of the polymerization procedures used in the prior art with any transition metal based catalyst systems can be employed with the present fluorenyl-containing metallocenes.

Generally the molar ratio of the aluminum in the aluminoxane to the transition metal in the metallocene would be in the range of about 0.1:1 to about $10^5$:1 and more preferably about 5:1 to about $10^4$:1. As a general rule, the polymerizations would be carried out in the presence of liquid diluents which do not have an adverse affect upon the catalyst system. Examples of such liquid diluents include propane, butane, isobutane, pentane, hexane, heptane, octane, cyclohexane, methylcyclohexane, toluene, xylene, and the like. The polymerization temperature can vary over a wide range, temperatures typically would be in the range of about −60° C. to about 280° C., more preferably in the range of about 20° C. to about 160° C. Typically the pressure would be in the range of from about 1 to about 500 atmospheres or greater.

The polymers produced with this invention have a wide range of uses that will be apparent to those skilled in the art from the physical properties of the respective polymer. Some of the catalysts are useful for preparing syndiotactic polymers. The term syndiotatic polymer as used herein is intended to include those polymers having segments of more than 10 monomeric repeating units in which the alkyl group of each successive monomeric unit is on the opposite side of the plane of the polymer.

Preparation of symmetrical di-substituted fluorenyl compounds

As noted previously there are various procedures known in the art for preparing many symmetrical di-substituted fluorenyl compounds. The production of 2,7-dichlorofluorene can be carried out as disclosed by A. Roedig, Houben/Weyl 5/4 330–41, i.e, by contacting fluorene with chlorine in the presence of N-chlorosuccimide. The compound 2,7-dibromofluorene can be obtained by bromination of fluorene in $CHCl_3$ or $CH_2Cl_2$ at 0° C. using procedures generally as taught in *J. Am. Chem. Soc.*, 84, 1238–41 (1962); *Bull. Chem. Soc. Jp.*, 44, 1614–19 (1971); or *J. Chem. Soc.*, 43, 164–5 (1883). The compound 2,7-diiodofluorene can be obtained using the procedure described in *Helv. Chem. Acta*, 53, 1311–23 (1970). The diiodofluorene can be separated from monoiodofluorene by crystallization from hot THF or toluene. The compound 2,7-di-t-butylfluorene can be obtained using procedures of the type shown in *Synthesis*, 335–7 (1984) and *Bull. Chem. Soc. Jp.*, 59, 97–103 (1986).

Multistep procedures are known in the art for producing 2,7-dimethoxyfluorene. It has been surprisingly discovered that the compound can be produced in one step using the copper catalyzed methanolysis of 2,7-dibromofluorene using conditions similar to those disclosed in *Tetrahedron Letters*, 34, 1007–1010 (1993) involving the use of ethyl acetate and concentrated sodium methoxide solutions.

The compound 2,7-bis(dimethylphenylcarbyl) fluorene, which is believed to be a new compound, was prepared by reacting benzoic acid with fluorene in hot polyphosphoric acid at about 100° C. to yield 2,7-dibenzoylfluorene which is then reacted with trimethyl aluminum in boiling toluene.

The compound 2,7-di(1-cyclohex-1-enyl)fluorene can be prepared by first forming a Grignard reagent from 2,7-diiodofluorene and magnesium and bromoethane in THF by heating for several days in a Schlenk tube at about 60°–90° C. Then cyclohexanone is added. After acidic workup in hot toluene, the 2,7-dicyclohexenyl fluorene is obtained.

A new shorter preparation of 2,7-substituted alkyl and aryl fluorenes is a further invention. The examples of substituents include methyl through cyclohexyl and even sterically strained mesityl or naphthyl moietys. The process involves reacting 2,7-diiodofluorene in diethyl ether with the appropriate Grignard reagent. Generally, it is desirable to use nickle phosphine, i.e. Ni(dppp)Cl$_2$, as a catalyst for the crossed coupling reaction. Literature references disclosing similar uses of the nickle phosphine are disclosed in *Pure Appl. Chem.*, 52; 669–79 (1980); *J. Chem. Soc.*, 1490–4 (1962); and *Inorg. Chem.*, 5, 1968–74 (1966). The liquid diluent for the reaction can vary over a wide range depending upon the results desired. Typical liquid diluents include tetrahydrofuran, diethylether, toluenes, and the like. Isolation is generally made by acidic hydrolysis and extraction with boiling toluene.

Examples of 2,7-substituted fluorenes that can be produced include 2,7-dicyclohexylfluorene; 2,7-dimethylfluorene; 2,7-diisopropylfluorene; 2,7-diphenylfluorene; 2,7-di(1-naphthyl) fluorene; 2,7-di(4-methylphenyl) fluorene; 2,7-di(2,4-dimethylphenyl) fluorene; 2,7-di(mesityl)fluorene, 2,7-di(4-fluorophenyl) fluorene; and the like.

Other routes are available for producing 2,7-substituted fluorene compounds. The compound 2,7-diacetylfluorene can be obtained by the acetylation of fluorene with acetic anhydride and aluminum trichloride. In the prior art such reactions have been conducted in 1,2-dichloroethane. It has now been discovered that even higher yields can be obtained by using the more safe solvent methylene chloride. A hydrogen reduction of the diacetylfluorene with Pd on carbon results in 2,7-diethylfluorene. On the other hand, the reaction of the diacetyl with trimethyl aluminum results in 2,7-di-t-butylfluorene. This new technique is superior to the prior art technique involving t-butylation of fluorene with butyl cresol in that it is more selective to the 2,7 isomer.

An improved shortened process for preparing 4,5-dimethylfluorene involves reacting fuming nitric acid with m-toluic acid to form 3-methyl-2-nitrobenzoic acid which is reduced to 2-amino-3-methyl benzoic acid. Preferably the reduction is carried out using hydrogen and a Pd on carbon catalyst. Diazotization and coupling of that product results in 6,6'-dimethyldiphenic acid which can then be cyclized using polyphosphoric acid to form 4,5-dimethylfluorenone which in turn can be hydrogenated over palladium on carbon to form 4,5-dimethylfluorene.

The compound 3,6-di-t-butylfluorene can be prepared with greater selectivity than prior art methods by brominating 4-t-butyl toluene and reacting that product with magnesium in THF using a Ni(tpp)$_2$Cl$_2$ catalyst. A preferred method for carrying out the bromination involves using an excess of N-bromosuccimide in CCl$_4$ together with subsequent hydrolysis of the crude product with CaCO$_3$ in water/dioxane. The coupled substituted biphenyl product is then subjected to oxidation with KMnO$_4$ in aqueous acetone. Ring closure is then effected by using hot polyphosphoric acid. The undesired by-products are separated by extraction using an ether/aqueous carbonate solution. The recovered 3,6-di-t-butylfluorenone is then hydrogenated using a palladium on carbon catalyst.

A further understanding of the present invention, its various aspects, objects and advantages will be provided by the following examples.

In the following examples where information is given about the microstructure of polymers as determined by $^{13}$CNMR, the spectra were taken using standard accepted spectroscopy techniques. The polymer was dissolved in trichlorobenzene and the spectra was taken with respect to an internal standard relative to hexamethylsiloxane which has a known reference point relative to tetramethyl silane. From the observed integrals of the relevant peaks, the details regarding the microstructure are calculated.

| | |
|---|---|
| Meso Content = | (mm) + ½ (mr) |
| Racemic Content = | (rr) + ½ (mr) |
| Isotacticity = | % (mm) |
| Heterotacticity = | % (mr) |
| Syndiotacticity = | % (rr) |
| Randomness Index = | $\dfrac{(mr)100}{2(m)(r)}$ |
| Average Isotactic Block Length = | $1 + \dfrac{2(mm)}{(mr)}$ |
| Average Syndiotactic Block Length = | $1 + \dfrac{2(rr)}{(mr)}$ |

For more detail regarding the determination of these values, reference can be made to Chapter 3 of the aforementioned book by Frank A. Bovey.

EXAMPLES

Example I

Preparation of 1-bromo-2-(fluorenyl)ethane

In this reaction, 8.3 g (0.05 m) of fluorene was dissolved in 150 ml of tetrahydrofuran. The 31.8 ml (0.05 m) of butyl lithium (1.6 molar in hexane) was added dropwise to this solution. After one hour, this solution was added gradually to a stirred solution of 9 ml (0.1 m) of dibromoethane in 300 ml of pentane within 2 hours. Then the reaction mixture was treated with 50 ml of an aqueous NH$_4$Cl solution, and then washed with 50 ml of water. The organic phase was dried over Na$_2$SO$_4$. Then the solvent was removed in vacuo. The yellow residue was dissolved in pentane. The pentane solution was filtered over silica. The solution was concentrated to about 20% of the original volume and then the product was crystallized at −30° C. A yield of 10.88 g of 1-bromo-2-(fluorenyl)ethane was obtained. The product was characterized through $^1$H NMR, $^{13}$C NMR, and Mass spectroscopy.

Example II

Reactions similar to that set forth in Example I have been carried out substituting other dihalo alkylenes for 1,2-dibromo ethane. Examples include 1,3-dibromopropane, 1,2-di-bromomethane, 1,2-dibromo-2-methyl ethane, and dichloromethane. The corresponding fluorenyl alkyl halides were obtained.

Example III

Cyclopentadiene was reacted with butlyl lithium in tetrahydorofuran to yield cyclopentadienyl lithium. A solution of 0.002 m cyclopentadienyl lithium in 150 ml of tetrahydrofuran at (−40 degrees C.) and a solution of 1-bromo-2-(fluorenyl)ethane in 50 ml of THF were mixed together at room temperature. Then 10 ml of hexamethyl phosphine triamide (HMPT) was added. After three hours stirring at room temperature, this solution was washed with 50 ml of aqueous NH4Cl solution, then washed with 50 ml of water, and then the organic phase was dried over Na2SO4. The solvent was removed in vacuo. The resulting 1-(fluorenyl)-2-cyclopentadienyl ethane can be purified by dissolving in pentane and then crystallizing. The product was characterized by mass spectroscopy and gas chromatography.

Example IV

Reactions similar to that set forth in Example III were carried out substituting other fluorenyl bromo alkanes for the fluorenyl bromo ethanes. Examples of the other bromo alkanes used included 1-fluorenyl-3-bromo propane, 1-(2,7-di-tert-butyl fluorenyl)-1-bromo methane, and 1-methyl-2-fluorenyl-1-bromo ethane. The corresponding alkyl bridged fluorenyl-cyclopentadienyl compounds were obtained. Also using a reaction similar to that of Example III but without the HMPT 2,7-di-tert-butyl fluorene was substituted for cyclopentadiene. The product 1-(2,7-di-tert-butyl fluorenyl)-2-fluorenyl ethane was recovered.

Example V

A number of fluorenyl-containing metallocenes were prepared using either diethyl ether or toluene as a solvent.

When diethyl ether was used as a solvent, about 1 millimole of the respective bridged or unbridged fluorenyl compound was dissolved in 200 milliliters of ether. Then 1.6 molar methyllithium in diethyl ether was added to the solution to provide 1 millimole of methyllithium for each millimole of cyclopentadienyl-type radical. (An exception would be in the case in which it was desired to produce a mono-valent salt of a bridged fluorenyl compound. In such a case then only about 0.5 millimole of methyl lithium would be used for each millimole of cyclopentadienyl-type radicals.) The reaction mixture was stirred until no additional methane gas was evolved. This was done at room temperature. Next the transition metal halide was added in small portions to the solution of the fluorenyl salt. The amount of transition metal was about 0.5 millimoles when the fluorenyl compound was a monovalent salt and about 1 millimole when the fluorenyl compound was a divalent salt. The resulting solution was typically stirred for an additional 30 minutes and then concentrated to about 50 milliliters and filtered. The orange to red-colored solids remaining on the filter plate were dissolved in dichloromethane and the resulting solution was concentrated and recrystallized, generally at about −78° C.

In the runs prepared using toluene as the solvent, about 1 millimole of the bridged or unbridged fluorenyl compound was mixed in 250 milliliters of toluene. This was combined with methyllithium (1.6 molar in diethyl ether) in an amount sufficient to provide 1 millimole of methyllithium for the umbridged compounds and 2 millimoles of the methyllithium for the bridged fluorenyl compounds. (Again the exception discussed in the previous paragraph also applies.) Then the reaction mixture was heated at reflux until no more methane gas was being released. The solution was then allowed to cool to room temperature. The transition metal halide was then slowly added to the solution. Again, about 0.5 millimoles of transition metal compound was employed with the divalent fluorenyl salts and about 1 millimole was employed with the monovalent fluorenyl salts. The suspension was then stirred for about 30 minutes. The solution was then concentrated to about 50 to 75 milliliters and filtered. The orange to red solids on the filter plate were dissolved in dichloromethane and the resulting solution was concentrated and cooled to −78° C. to obtain the metallocene as a solid precipitate.

Procedures of those general types have been used to prepare the following metallocenes:

(1,2-difluorenyl ethane)zirconium dichloride; (1-fluorenyl-2-indenyl ethane)zirconium dichloride and hafnium dichloride; (1-fluorenyl-1-cyclopentadienyl methane)zirconium dichloride; (1-fluorenyl-1-cyclopentadienyl methane)zirconium trichloride, (1,2-di(2-tert butyl fluorenyl)ethane)zirconium dichloride and hafnium dichloride; (1,2-di(2-methyl fluorenyl)ethane)zirconium dichloride; (1,2-difluorenyl ethane)hafnium dichloride; bis(2,7-di-tert butyl-4-methyl fluorenyl)zirconium dichloride; (1,3-difluorenyl propane)zirconium dichloride and hafnium dichloride; (1-fluorenyl-2-methyl-2-fluorenyl ethane)zirconium dichloride; dimethyl silyl difluorenyl zirconium dichloride; (1,2-di(1-methyl fluorenyl)ethane)zirconium dichloride; (1,2-di(1-tert butyl fluorenyl)ethane)zirconium dichloride and hafnium dichloride; (1,2-di(2-ethyl fluorenyl)ethane zirconium dichloride and hafnium dichloride; (1,2-di(4-tert butyl fluorenyl)ethane zirconium dichloride; (1-fluorenyl-2-cyclopentadienyl ethane)zirconium dichloride; (1-fluorenyl-2-(3-methylcyclopentadienyl)ethane zirconium dichloride; (1-fluorenyl-3-indenyl propane)zirconium dichloride; (1-fluorenyl-2-methyl-2-cyclopentadienyl ethane)zirconium dichloride; (1-fluorenyl-2-methy-2-indenyl ethane)zirconium dichloride; (1-fluorenyl-2-methyl-2-(3-methylcyclopentadienyl)ethane)zirconium dichloride; (1-(1-methyl fluorenyl)-2-(4-methyl fluorenyl)ethane)zirconium dichloride; (1-(1-tert butyl fluorenyl)-2-(4-tert butyl fluorenyl)ethane) zirconium dichloride; bis(2,7-di-tert butyl-4-methyl fluorenyl)zirconium dichloride; (1,2-difluorenyl ethane) vandium dichloride, (1,1-difluorenyl methane) vandium dichloride, bis(1-methyl fluorenyl)zirconium dichloride; bis(1-methyl fluorenyl)hafnium dichloride; bis(2-ethyl fluorenyl)zirconium dichloride; bis (4-methyl fluorenyl)zirconium dichloride, and bis(4-methyl fluorenyl)hafnium dichloride.

Use of Fluorenyl Metallocenes

A number of fluorenyl-containing metallocenes prepared in accordance with the present invention were evaluated for their effectiveness as catalysts for the polymerization of olefins. The specific metallocenes evaluated are referred to in the following tables as follows:

| Catalyst | |
|---|---|
| A | (1,2-diflorenyl ethane) zirconium dichloride |
| B | (1-fluorenyl-2-indenyl ethane) zirconium dichloride |
| C | (1-fluorenyl-1-cyclopentadienyl methane) zirconium dichloride |
| D | (1,2-di(2-tertbutyl fluorenyl)ethane) zirconium dichloride |
| E | bis (2,7-tertbutyl-4-methyl fluorenyl) zirconium dichloride |
| F | (1-fluorenyl-1-cyclopentadienyl methane) zirconium trichloride |
| H | (1-fluorenyl-2-methyl-2-indenyl ethane) zirconium dichloride |
| I | (1,2-difluorenyl ethane) hafnium dichloride |

The polymerizations were carried out in an autoclave type reactor using methylaluminoxane as a cocatalyst. The source of the methylaluminoxane varied. In some runs a 30 weight percent toluene solution obtained from Schering was used. In other runs a 10 weight percent toluene solution of the methylaluminoxane obtained from Ethyl Corp was used. In a dry box under substantially inert conditions the solid metallocene was added to a serum vial and then a known quantity of the metallocene solution was added to the vial. The gram atom ratio of the aluminum in the aluminoxane to the metal in the metallocene was about 2200 to 1. Some of the resulting catalyst system solutions were used in more than one polymerization. Accordingly, all the catalyst system solutions were not used immediately after preparation. For optimum results it is considered desirable to use the catalyst system soon after preparation.

The catalyst system solution was added to the polymerization reactor which had been suitably prepared for the particular polymerization to be conducted. Typically for the polymerization of propylene the reactor contained liquid propylene as the reaction diluent. For polymerizations of ethylene or 4-methyl-1-pentene liquid isobutane diluent was employed. After the catalyst was charged then monomer and hydrogen, if employed, was added at room temperature. The reaction was then allowed to proceed for a period of time at which the reactor was cooled in an attempt to maintain a selected reaction temperature. In most cases after the polymerization was complete the diluent was flashed off and the polymer solids recovered and characterized. In some cases where the polymer was of low molecular weight or substantially all in solution the liquid would be drained and the unreacted monomer, comonomer, and/or diluent removed by evaporation.

Various characteristics of the polymer and the polymerization were characterized. Examples of characteristics determined in various cases include density in grams/ml (ASTM D1505-68); Melt Flow Index in grams of polymer/10 minutes (ASTM D1238-65T, Condition L); High Load Melt Index in grams of polymer/10 minutes 190° C. (ASTM D1238, Condition E); Melt Index in grams of polymer/10 minutes 190° C. (ASTM D1238, Condition E); heptane insolubles determined by the weight percent of insoluble polymer remaining after extraction with boiling heptane; melting point in degrees centigrade by Differential Scanning Calorimetry; molecular weights by size exclusion chromatography, i.e. weight average molecular weight referred to herein as Mw and number average molecular weight referred to herein Mn; heterogenity index determined by dividing Mw by Mn. The (SEC) size exclusion chromatography was conducted using a linear column capable of resolving the wide range of molecular weights generally observed in polyolefins, such as polyethylene. The SEC used a 1,2,4-trichlorobenzene solution of the polymer at 140° C. The intrinsic viscosity was calculated from the SEC using the Mark-Houwink-Sakrada constants, i.e. $k \cdot MW^a$ in deciliters/gram, referred to in the following tables as IV. Unless indicated otherwise the conditions employed for characterizing the various properties were the same for each polymer evaluated. In some cases infrared and 13C NMR spectra were taken of the polymer. The NMR spectra were conducted on a 1,2,4-trichlorobenzene solution of the polymer. The base standard in the NMR spectra was 0 ppm based on tetramethylsilane.

Example VI

Ethylene polymerization With (1,2 difluorenylethane) zirconium dichloride

A number of polymerization runs were conducted to evaluate the effectiveness of (1,2-difluorenylethane) zirconium dichloride as a catalyst for the polymerization of ethylene both alone and with a comonomer. The various polymerization variables and the results are summarized in the following Table. The value reported for comonomer when used in all the following tables refers to grams of the comonomer, also yield is in grams.

TABLE I

| Run | Temp. °C. | Catalyst mg. | ΔPC2 | ΔPH2 | Hexene | Time | Yield | HLMI/MI | Density | Mw × 10³ | HI | IV |
|---|---|---|---|---|---|---|---|---|---|---|---|---|
| 1 | 90 | 0.66 | 70 | NA | NA | 20 | 29.7 | HLMI = 0 | 0.9384 | 633 | 3.9 | 5.79 |
| 2 | 70 | 0.66 | 70 | 25 | NA | 60 | 25.8 | 448/2.43 | 0.9732 | 114 | 21.8 | 1.32 |
| 3 | 70 | 1 | 70 | 25 | NA | 60 | 31.9 | 668/1.42 | 0.9759 | 116 | 19.4 | 1.34 |
| 4 | 70 | 1 | 50 | 25 | NA | 60 | 81 | 363.2/7.19 | 0.9698 | 71.9 | 10.6 | 7.1 |
| 5 | 90 | 0.66 | 70 | 2.7 | 90 | 60 | 8.15 | 5.1/.0042 | 0.8981 | 170 | 46.6 | 2.03 |
| 6 | 70 | 1.65 | 50 | NA | 90 | 70 | 161 | HLMI = 0.13 | 0.8881 | 332 | 16.8 | 3.52 |
| 7 | 70 | 3 | 135 | 10 | 50 | 45 | 130 | 288.5/0.5 | 0.9154 | 165 | 23.2 | 1.88 |
| 8 | 70 | 1 | 70 | 25 | 50 | 60 | 72.5 | 900/7.97 | 0.9297 | 159 | 27.1 | 1.8 |
| 9 | 70 | 1 | 70 | 25 | 25 | 60 | 62.1 | waxy | 0.9478 | 24.1 | 7.1 | 0.41 |
| 10 | 70 | 1 | 150 | 25 | 50 | 60 | 79 | 79.6 MI | 0.9307 | 53.5 | 8.9 | 0.79 |

The table demonstrates that the fluorenyl-containing metallocene is capable of producing polymers of ethylene having a wide range of properties. In the absence of hydrogen the polymer was a very high molecular weight material as evidenced by the low HLMI, i.e, High Load Melt Index. The data further demonstrates that copolymerization of ethylene and hexene can result in lower density polymers.

Example VII

Ethylene Polymerization with Various Bridged Fluorenyl Metallocenes

A number of ethylene polymerizations were also conducted using other bridged metallocenes. The various polymerization variables and the results are summarized in the following Table. Runs 4 and 5 from the previous Table are included for comparison.

that the polymer contains high levels of syndiotactic molecular structure.

TABLE II

| Run | Type Catalyst | Temp. | Catalyst, mg. | ΔPC2 | ΔPH2 | Hexene | Time | Yield | HLMI/MI | Density | Mw × 10³ | HI | IV |
|---|---|---|---|---|---|---|---|---|---|---|---|---|---|
| 4 | A | 70 | 1 | 50 | 25 | NA | 60 | 81 | 363.2/7.19 | 0.9698 | 7.9 | 10.6 | 7.1 |
| 11 | B | 70 | 1.4 | 50 | 25 | NA | 60 | 100 | 811.8/19.6 | 0.9727 | 4.7 | 6.6 | 0.78 |
| 12 | C | 70 | 1 | 70 | 25 | NA | 60 | 21 | 0.06 HLMI | 0.9517 | — | — | — |
| 13 | C | 70 | 2 | 250 | 25 | NA | 60 | 37 | 0.07 HLMI | 0.9568 | — | — | — |
| 14 | C | 70 | 2 | 70 | 3 | 90 | 60 | 137 | 18.3/0.15 | 0.8817 | 1.7 | 4.4 | 1.6 |
| 5 | A | 70 | 0.66 | 70 | 2.7 | 90 | 60 | 8.15 | 5.1/0.042 | 0.8981 | 1 | 56.6 | 2.03 |

The Table demonstates that (1-fluorenyl-2-indenyl ethane) zirconium dichloride, i.e. Catalyst B, and Catalyst C, i.e (1-fluorenyl-1-cyclopentadienyl ethane) zirconium dichloride are also suitable for the polymerization of ethylene. Catalyst C gave a higher molecular weight material as indicated by the HLMI values. Run 14 demonstrates that Catalyst C is also capable of producing a copolymer of ethylene and hexene. The particular copolymer produced in this run is particularly unusual in that in contained 12.4 mole percent comonomer and a relative comonomer dispersity of 105.9. The mole percent comonomer and relative comonomer dispersity were determined from NMR spectroscopy using the technique disclosed in U.S. 4,522,987, the disclosure of which is incorporated herein by reference. Such a polymer can be referred to as a low density super random copolymer, i.e. a polymer having a super random distribution of the comonomer.

Example VIII

Propylene Polymerization With Various Fluorenyl Metallocenes

A number of polymerizations of propylene were conducted using various fluorenyl-containing metallocenes. The reaction variables and the results are summarized in the following Table.

Run 20 demonstrates that Catalyst D, i.e. (1,2-di(2-tert butyl fluorenyl)ethane) zirconium dichloride can be used to produce a crystalline polypropylene.

Run 21 demonstrates that Catalyst E, i.e. the unbridged metallocene bis(2,7-di-tertbutyl-4-methyl fluorenyl) zirconium dichloride, produced only a small amount of solid polypropylene at 60° C. Run 22 shows that Catalyst E was not particularly effective at all at 23.4° C.

Run 23 and 24 employed a non-sandwich bonded metallocene, i.e. a metallocene in which only one of the cyclopentadienyl-type radicals was bonded to the transition metal. The catalyst produced only about 3 to 5 grams grams of solid polymer along with about 45 to 55 of low molecular weight propylene soluble polymer. Unless indicated otherwise by the formula or other means, all the bridged metallocenes referred to herein are sandwich bonded.

Run 26 employed the bridged metallocene (1-fluorenyl-2-indenyl ethane) zirconium dichloride. Although this catalyst yielded 460 grams of solid polymer 94.4 weight percent of the polymer was a low molecular weight xylene soluble polymer. Similarly, the bridged metallocene (1-fluorenyl-2-methyl-2-indenyl ethane) zirconium dichloride in Run 27 yielded 82 grams of solid, 88 weight percent of which was low molecular weight xylene soluble material.

TABLE III

| Run | Type Catalyst | Temp. °C. | Catalyst mg | ΔPH2 | Time | Yield | MF | Density | Mw × 10³ | HI | IV | Insolubles | M.P. °C. |
|---|---|---|---|---|---|---|---|---|---|---|---|---|---|
| 15 | C | 60 | 3 | NA | 30 | 360 | 19.6 | 0.8843 | 83.3 | 3.6 | 0.78 | 96.6 | 132.6 |
| 16 | C | 60 | 1 | NA | 60 | 230 | 14.6 | 0.8812 | 94 | 4.3 | 0.86 | 92.4 | 133.6 |
| 17 | C | 60 | 1 | 3.5 | 60 | 431 | 15.6 | 0.8829 | 89.3 | 2.3 | 0.83 | 98.1 | 134.6 |
| 18 | C | 70 | 1 | 10 | 60 | 400 | 27 | 0.8797 | 74.8 | 2.1 | 0.72 | 78.5 | 134.8 |
| 19 | C | 70 | 1 | 5 | 60 | 16 | wax | — | — | — | — | 94.7 | 133 |
| 20 | D | 60 | 2.3 | NA | 50 | 270 | — | <0.8740 | 51.6 | 2.5 | 0.55 | 93.4 | — |
| 21 | E | 60 | 1.6 | 10 | 60 | 9.5 | — | — | — | — | — | — | — |
| 22 | E | 23.4 | 1.6 | 0 | 60 | 0 | — | — | — | — | — | — | — |
| 23 | F | 70 | 2.5 | 25 | 60 | 3 | — | — | — | — | — | — | — |
| 24 | F | 70 | 2.5 | 25 | 60 | 5 | — | — | — | — | — | — | — |
| 26 | B | 70 | 5 | 10 | 60 | 460 | — | — | — | — | — | — | — |
| 27 | H | 70 | 2 | 10 | 60 | 82 | — | — | — | — | — | — | — |
| 28 | A | 70 | 3 | 10 | 5 | 30 | — | — | — | — | — | — | — |
| 29 | I | 70 | 5.2 | 10 | 60 | 182 | — | — | — | — | — | — | — |

Table III demonstrates that Catalyst C, i.e. (1-fluorenyl-1-cyclopentadienyl methane) zirconium dichloride, can be used to produce a polymer from propylene. The data in runs 15–17 shows that the polypropylene is highly crystalline as demonstrated by the heptane insolubles values. It is believed Runs 28 and 29 employed bridged metallocenes based on 1,2-difluorenyl ethane. Both the zirconium and the hafnium metallocenes yielded solid polypropylene.

Example IX

Catalyst C, i.e. (1-fluorenyl-1-cyclopentadienyl methane) zirconium dichloride, was evaluated as a catalyst for the polymerization of 4-methyl-1-pentene. The amount of the metallocene employed was 5 mg. The polymerization was conducted in the presence of hydrogen with the differential pressure of the hydrogen being 25. The polymerization temperature was 120° C. and the length of the polymerization was 2 hours. The polymerization resulted in the production of 96.7 grams of a solid having a weight average molecular weight of 33,330; a heterogenity index of 1.8; and a calculated intrinsic viscosity of 0.12. About 92 weight percent of the solid was insoluble in boiling heptane. The polymer had a melting point of 197.9° C. A 13C NMR spectrum was taken of the polymer as recovered, i.e. without heptane solubles removed, and it indicated that the polymer contained a substantial amount of syndiotactic functionality. A copy of the $^{13}$C NMR spectrum is provided in FIG. 1. Significant peaks were observed at about 22.8, 24.8, 26, 31.8, 42.8, 43.1, 46.1, and 46.2 ppm. The intensity of the peak at 43.1 ppm has greater than 0.5 of the total peak intensities in the range of 42.0 and 43.5 ppm. The peak at about 46.2 ppm had a greater intensity than any peak between the major peaks at 46.1 and 43.1 ppm. Further, the peak at about 42.8 ppm had a greater intensity than any peak between the major peaks at 46.1 and 43.1 ppm. These peak locations are relative to a peak of zero ppm for tetramethylsilane.

Example X

Under conditions substantially as used in Example VIII, a run was carried out attempting to polymerize 4-methyl-1-pentene with Catalyst A, i.e. the bridged catalyst (1,2-difluorenyl ethane) zirconium dichloride. In this case 7 mg of the catalyst was employed and 180 grams of solid atactic wax-like polymer was obtained.

A similar run was conducted substituting the unbridged metallocene, bis(2-methylfluorenyl) zirconium dichloride for Catalyst A in the polymerization of 4-methyl-1-pentene. In this run 5 mg of the metallocene was used and 9.7 grams of solid polymer was recovered. Two samples of the polymer were subjected to heptane extraction. The extraction gave heptane insoluble values of 54.8 and 68.8. The catalyst was thus not as active as either the bridged Catalyst mentioned in the preceding paragraph or bridged Catalyst A.

Example XI

Polymerizations were carried out to compare the effects of different metallocenes on the polymerization of propylene. The polymerizations were conducted under particle form conditions using propylene as the diluent. The metallocene was used in conjunction with methylaluminoxane cocatalyst. Polymerizations were conducted both with and without hydrogen. Each polymerization involved weighing a metallocene in a dry box and dissolving it in a 10% solution of methylaluminoxane and toluene obtained from Schering AG. The aluminum to zirconium molar ratio was 1,000/1. The charge order was metallocene/MAO, 15 psi hydrogen as measured as the pressure dropped on a 300 cc cylinder (when used), and two-thirds of a gallon of liquid propylene. After heating these materials to 70° C., the content of the reactor was stirred at that temperature for one hour. The polymerization was then terminated by venting off surplus propylene. The polymer was recovered, dried and weighed to determine the yields. The results are summarized in Table IV.

TABLE IV

| Run No. | Metallocene | Activity g PP/mol Zr | $M_w$ | $M_w/M_n$ | [r] % | [m] % | [rr] % | [mm] % | [mr] % | MF |
|---|---|---|---|---|---|---|---|---|---|---|
| 30 | [(Flu)(Cp)CH$_2$]ZrCl$_2$-A | 2.75 × 10$^8$ | 71310 | 1.82 | 93.47 | 6.53 | 89.60 | 2.67 | 7.73 | 70.7 |
| 31 | [(Flu)(Cp)CH$_2$]ZrCl$_2$-B | 0.86 × 10$^8$ | 67780 | 1.91 | 93.48 | 6.52 | 89.49 | 2.53 | 7.73 | 99.9 |
| 32 | [(Flu)(Cp)Me$_2$C]ZrCl$_2$-A | 1.70 × 10$^8$ | 83220 | 2.36 | 93.06 | 6.94 | 89.01 | 2.89 | 8.10 | 37.9 |
| 33 | [(Flu)(Cp)Me$_2$C]ZrCl$_2$-B | 0.64 × 10$^8$ | 83000 | 2.14 | 92.40 | 7.60 | 87.89 | 3.09 | 9.02 | 41.8 |
| 34 | [(2,7 Me Flu)(Cp)Me$_2$C]ZrCl$_2$-A | 1.18 × 10$^8$ | 93180 | 2.18 | 92.64 | 7.36 | 87.73 | 2.44 | 9.84 | 24.8 |
| 35 | [(2,7 Me Flu)(Cp)Me$_2$C]ZrCl$_2$-B | 0.21 × 10$^8$ | 86700 | 2.70 | 91.03 | 8.97 | 85.30 | 3.25 | 11.44 | 24.0 |
| 36 | [(2,7 t-Bu Flu)(Cp)Me$_2$C]ZrCl$_2$-A | 2.12 × 10$^8$ | 75590 | 2.15 | 94.75 | 5.25 | 91.49 | 1.99 | 6.52 | 72.0 |
| 37 | [(2,7 t-Bu Flu)(Cp)Me$_2$C]ZrCl$_2$-B | 1.28 × 10$^8$ | 71850 | 2.01 | 93.49 | 6.51 | 89.59 | 2.60 | 7.80 | 84.1 |
| 38 | [(2,7 Ph Flu)(Cp)Me$_2$C]ZrCl$_2$-A | 1.43 × 10$^8$ | 91170 | 2.86 | 93.43 | 6.57 | 88.94 | 2.09 | 8.97 | 33.4 |
| 39 | [(2,7 Ph Flu)(Cp)Me$_2$C]ZrCl$_2$-B | 0.12 × 10$^8$ | 81540 | 2.29 | 92.74 | 7.26 | 87.66 | 2.18 | 10.16 | 96.3 |
| 40 | [(2,7 Ph Flu)(Cp)Ph$_2$C]ZrCl$_2$-A | 1.86 × 10$^8$ | 212980 | 5.44 | 92.76 | 7.24 | 88.16 | 2.63 | 9.21 | 0.21 |
| 41 | [(2,7 Ph Flu)(Cp)Ph$_2$C]ZrCl$_2$-B | 0.13 × 10$^8$ | 257640 | 3.58 | 91.67 | 8.33 | 86.22 | 2.88 | 10.90 | 0.69 |
| 42 | [(2,7 Br Flu)(Cp)Me$_2$C]ZrCl$_2$-A | 0.44 × 10$^8$ | 56420 | 2.72 | 90.62 | 9.38 | 84.73 | 3.49 | 11.78 | 131.0 |
| 43 | [(2,7 Br Flu)(Cp)Me$_2$C]ZrCl$_2$-B | 0.18 × 10$^8$ | 53600 | 2.81 | 90.47 | 9.53 | 84.44 | 3.51 | 12.05 | 156.7 |
| 44 | [(2,7 t-Bu Flu)(Cp)Ph$_2$C]ZrCl$_2$-A | 4.72 × 10$^8$ | 103830 | 2.20 | 95.21 | 4.79 | 92.09 | 1.67 | 6.24 | 0.41 |
| 45 | [(2,7 t-Bu Flu)(Cp)Ph$_2$C]ZrCl$_2$-B | 0.12 × 10$^8$ | 111490 | 2.20 | 93.67 | 6.29 | 89.41 | 2.06 | 8.53 | 0.16 |

Runs 30–33 are control run employing unsubstituted fluorenyl-containing metallocenes. The table shows that all the fluorenyl metallocened produced highly syndiotactic polypropylene.

In the table, the letter A after the metallocene refers to runs made with hydrogen and the letter B after the metallocene structure refers to runs made without hydrogen. With the exception of the metallocene used in Runs 40 and 41, all the metallocenes produced a very unusual effect in that the polymers produced without hydrogen had a lower molecular weight than those produced with hydrogen. A polypropylene produced with (2,7-dimethylfluorenyl)(cylcopentadienyl) dimethylmethane zirconium dichloride in Runs 34 and 35 produced a polymer having slightly higher molecular weight than those produced under the same conditions with the two control metallocenes.

The metallocene (2,7-di-butylfluorenyl)(cyclopentadienyl) dimethylmethane zirconium dichloride of Runs 36 and 37 was a much more active catalyst than the comparable control catalyst of Runs 32 and 33 which had no substituents on the fluorenyl portion. The inventive catalyst of Runs 36 and 37 also produced a higher level of syndiotacticity than the control catalyst of Runs 32 and 33.

The metallocene (2,7-di-phenylfluorenyl)(cyclopentadienyl) dimethylmethane zirconium dichloride of Runs 38 and 39 was somewhat less active than the catalyst of Runs 37 and 38; however, it did result in a higher molecular weight polymer. However, the percent r, i.e. racemic content was somewhat higher than that obtained with the control catalyst of Runs 32 and 33.

The metallocene (2,7-di-phenylfluorenyl)(cyclopentadienyl) diphenylmethane zirconium dichloride produced a remarkably much higher molecular weight polymer than any of the other metallocenes in the study.

The metallocene (2,7-dibromofluorenyl)(cyclopentadienyl) dimethylmethane zirconium dichloride of Runs 42 and 43 gave the lowest percent syndiotacticity for those tested. The polymer also had a much higher melt flow and a lower molecular weight.

The metallocene (2,7-di-t-butylfluorenyl)(cyclopentadienyl) diphenylmethane zirconium dichloride of Runs 44 and 45 is particularly interesting in that the addition of 15 psi hydrogen increased the activity of the catalyst about 39 fold without causing much change in the molecular weight of the polymer. This catalyst is also of particular interest in that most of the polymer produced was in the form of spherical particles. This is particularly surprising since the polymerizations were conducted with a homogeneous, i.e. soluble catalyst system, without the presence of any support.

That which is claimed is:

1. A metallocene of the formula R"(FlR$_n$)(CpR$_m$)MeQ$_k$, wherein Fl is a fluorenyl radical, Cp is a cyclopentadienyl, indenyl, tetrahydroindenyl, or fluorenyl radical, each R of Cp is the same or different and is an organo radical having 1 to 20 carbon atoms, R" is a $C_1$ to $C_{20}$ hydrocarbyl structural bridge linking (FlR$_n$) and (CpR$_m$), Me is a metal selected from the group consisting of IVB, VB, and VIB metals of the Periodic Table, each Q is the same or different and is selected from the group consisting of hydrocarbyl or hydrocarbyloxy radicals having 1 to 20 carbon atoms and halogen, k is a number sufficient to fill out the remaining valences of Me, m is a number in the range of 0 to 7, n is a number in the range of 2 to 7 and (FlR$_n$) is symmetrically substituted with identical substituents, said substituents being selected from the group consisting of methyl vinyl and hydrocarbyl radicals having up to 20 carbon atoms, said hydrocarbyl radicals being selected from a group consisting of cycloalkyl, cycloalkenyl, aralkyls and aryl radicals.

2. A metallocene according to claim 1 wherein n is 2 and each R on (FlR$_n$) is methyl vinyl.

3. A metallocene according to claim 1 wherein n is 2 and each R on (FlR$_n$) is a cycloalkene.

4. A metallocene according to claim 1 wherein n is 2 and each R on (FlR$_n$) is cyclohex-1-enyl.

5. A metallocene according to claim 1 wherein n is 2 and each R on (FlR$_n$) is aryl.

6. A metallocene according to claim 5 wherein each R on (FlR$_n$) is an aryl radical selected from the group consisting of phenyl; 1-naphthyl; 4-methylphenyl; 2,4-dimethylphenyl; and mesityl.

7. A metallocene according to claim 6 wherein the R groups on (FlR$_n$) are at the 2 and 7 positions of Fl.

8. A metallocene according to claim 7 wherein each R on (FlR$_n$) is a phenyl radical.

9. A metallocene according to claim 8 wherein (CpR$_m$) is unsubstituted cyclopentadienyl.

10. A metallocene according to claim 9 wherein R" is indanylidene.

11. A metallocene according to claim 10 wherein R" is 1,1-diphenylmethane.

12. A metallocene according to claim 7 wherein R" is cyclopentylidene and each R on (FlR$_n$) is aryl.

13. A metallocene according to claim 1 wherein n is 2 and each R on (FlR$_n$) is dimethyl phenyl carbyl.

14. A metallocene according to claim 13 wherein R" is 1,1-diphenylmethane.

15. A process for polymerizing an alpha olefin having at least three carbon atoms comprising contacting said olefin under suitable polymerization conditions with a catalyst system comprising a metallocene of claim 1 and a suitable cocatalyst.

16. A process according to claim 15 wherein the R substituents of (FlR$_n$) are at the 2 and 7 positions and are cyclohexyl radicals.

17. A process for producing a homopolymer of propylene comprising contacting propylene under suitable polymerization conditions with a catalyst system comprising a fluorenyl-containing metallocene and a suitable cocatalyst, said metallocene being selected from the group consisting of 1-(2,7-diphenylfluorenyl)-1-(cyclopentadienyl)-1,1-(diphenyl) methane zirconium dichloride and 1-(2,7-di-t-butylfluorenyl)-1-(cyclopentadienyl)-1,1-(diphenyl) methane zirconium dichloride.

18. A process according to claim 17 wherein said cocatalyst comprises an alkylaluminum.

19. A process according to claim 18 wherein the metallocene 1-(2,7-diphenylfluorenyl)-1-(cyclopentadienyl)-1,1-(diphenyl) methane zirconium dichloride is employed.

20. A process according to claim 18 wherein the metallocene 1-(2,7-di-t-butyl fluorenyl)-1-(cyclopentadienyl)-1,1-(diphenyl)methane zirconium dichloride is employed.

21. A process according to claim 17 wherein the metallocene 1-(2,7-diphenylfluorenyl)-1-(cyclopentadienyl)-1,1-(diphenyl) methane zirconium dichloride is employed.

22. A process according to claim 17 wherein the metallocene 1-(2,7-di-t-butyl fluorenyl)-1-(cyclopentadienyl)-1,1-(diphenyl) methane zirconium dichloride is employed.

* * * * *

UNITED STATES PATENT AND TRADEMARK OFFICE
CERTIFICATE OF CORRECTION

PATENT NO. : 5,571,880

DATED : November 5, 1996

INVENTOR(S) : Helmut G. Alt et al

It is certified that error appears in the above-identified patent and that said Letters Patent is hereby corrected as shown below:

Column 20, claim 11, line 1, "10" should be changed to ---9---.

Signed and Sealed this

Twenty-eighth Day of January, 1997

Attest:

BRUCE LEHMAN

Attesting Officer    Commissioner of Patents and Trademarks